United States Patent
Warchol et al.

(10) Patent No.: US 7,906,071 B2
(45) Date of Patent: Mar. 15, 2011

(54) FLAME PHOTOMETRIC DETECTOR HAVING IMPROVED SENSITIVITY

(75) Inventors: Andrew Martin Warchol, Wilmington, DE (US); Bruce Douglas Quimby, Lincoln University, PA (US); W. Dale Snyder, West Chester, PA (US); Paul Craig Dryden, West Grove, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1180 days.

(21) Appl. No.: 11/034,017

(22) Filed: Jan. 12, 2005

(65) Prior Publication Data

US 2006/0153734 A1     Jul. 13, 2006

(51) Int. Cl.
*G01N 33/00* (2006.01)

(52) U.S. Cl. ........ 422/54; 422/50; 422/68.1; 422/82.05; 422/82.09

(58) Field of Classification Search ............ 422/50, 422/54, 68.1, 82.05, 82.09
See application file for complete search history.

(56) References Cited

U.S. PATENT DOCUMENTS

| | | | |
|---|---|---|---|
| 3,489,498 A | 1/1970 | Brody et al. | |
| 5,052,805 A | 10/1991 | Sides | |
| 5,153,673 A | 10/1992 | Amirav | |
| 5,424,217 A * | 6/1995 | Benner et al. | 436/123 |
| 5,708,507 A * | 1/1998 | Wright et al. | 356/417 |

FOREIGN PATENT DOCUMENTS

| | | |
|---|---|---|
| GB | 711924 | 2/1952 |
| GB | 2064763 | 11/1980 |
| GB | 2352034 | 3/1998 |
| WO | WO89/03980 | 10/1987 |

* cited by examiner

*Primary Examiner* — Sam P Siefke (57) ABSTRACT

A flame photometric detector comprises a burner assembly configured to combust a sample of an effluent, the combusted sample emitting at least one excited molecule, an interchangeable selective optical filter configured to pass a plurality of selected optical wavelengths corresponding to the excited molecule, and a photomultiplier tube configured to quantify the concentration of the excited molecule.

16 Claims, 7 Drawing Sheets

FLAME PHOTOMETRIC DETECTOR HAVING IMPROVED SENSITIVITY

BACKGROUND

Gas chromatography is used to analyze and detect the presence of many different substances in a gaseous sample. Gas chromatography uses various types of detectors, depending on the specific element or compound sought to be detected. Different detectors are used to achieve selective and/or highly sensitive detection of specific elements or compounds, in particular chromatographic analyses.

Typically, a flame photometric detector is used to detect the presence of sulfur or phosphorous in a particular sample, or analyte. A flame photometric detector uses what is referred to as a chemiluminescent reaction where compounds containing sulfur or phosphorous encounter a hydrogen-rich flame. Chemiluminescence uses quantitative measurements of the optical emission from excited chemical species to determine analyte concentration. Chemiluminescence is typically emission from energized molecule species. When burned, or combusted, in such a flame, sulfur is transformed into an emitting species referred to as "$S_2$," and phosphorous is transformed into an emitting species referred to as "HPO." The emission wavelength range for excited $S_2$ includes, among others, the region from 320-405 nanometers (nm) and the wavelength range for excited HPO includes, among others, the range from 510-530 nm. The molecular emissions impinge on a photomultiplier tube, which converts photons to an electrical signal to quantify the concentration of a particular excited species.

To selectively detect either the excited $S_2$ emission or the excited HPO emission, a narrow band-pass optical (interference) filter has typically been used between the flame and the photomultiplier tube to isolate the appropriate emission band. Unfortunately, a narrow band-pass optical filter limits the signal-to-noise ratio, and therefore the signal strength of the signal delivered to the photomultiplier, resulting in an inability to detect minute quantities of an analyte. For example, a narrow band-pass optical filter used in a conventional flame photometric detector to detect sulfur transmits a photon emission band ranging in wavelength from 385-400 nm and has 65% transmissivity. A disadvantage of such an optical filter is that it only passes one of many characteristic emission bands for sulfur, thereby limiting the signal supplied to the photomultiplier tube. Further, to detect the presence of different analytes, different filters must be interchanged.

Therefore, it would be desirable to detect the presence of multiple elements without having to change interference filters in a flame photometric detector.

SUMMARY OF THE INVENTION

According to one embodiment, a flame photometric detector comprises a burner assembly configured to combust a sample of an effluent, the combusted sample emitting at least one excited molecule, an interchangeable selective optical filter configured to pass a plurality of selected optical wavelengths corresponding to the excited molecule and a photomultiplier tube configured to quantify the concentration of the excited molecule.

Other aspects and advantages of the invention will be discussed with reference to the figures and to the detailed description of the preferred embodiments.

BRIEF DESCRIPTION OF THE FIGURES

The invention will be described by way of example, in the description of exemplary embodiments, with particular reference to the accompanying figures in which.

DETAILED DESCRIPTION

While described below for use in detecting sulfur and phosphorous, the selective optical filter for use in a flame photometric detector can be modified to detect the presence of other elements. For example, by carefully designing the transmissive and non-transmissive wavelengths of a selective optical filter in accordance with embodiments of the invention, the presence of other elements can be detected and analyzed. Further, while particular wavelengths are described herein, the selective optical filter described below can be configured to be transmissive and non-transmissive for other wavelengths.

Figure 1:
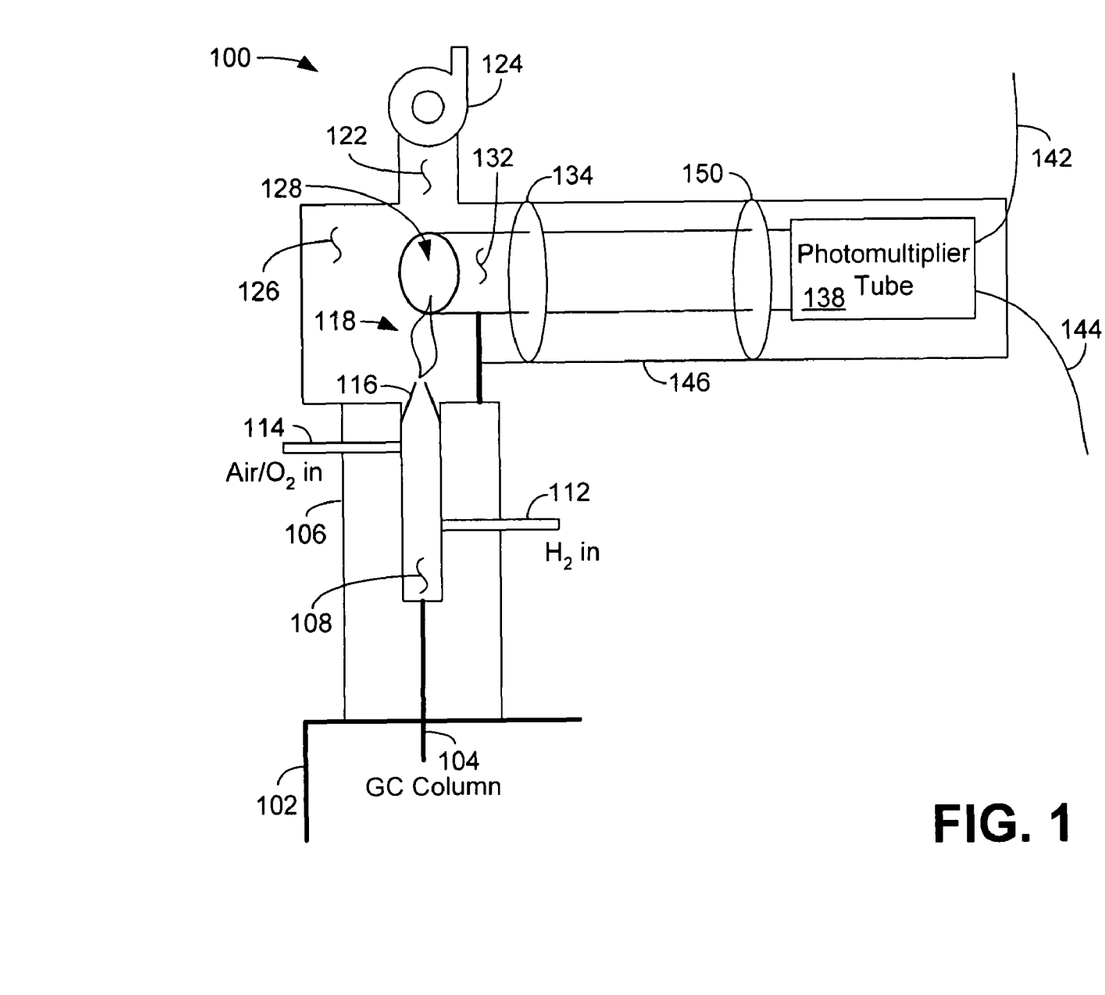
FIG. 1 is schematic diagram illustrating a flame photometric detector employing a selective optical filter.

FIG. 1 is a schematic diagram illustrating a flame photometric detector 100 employing a selective optical filter. The flame photometric detector 100 generally includes a body portion 146 and a sample supply element 106. In one embodiment, the output of a gas chromatograph, illustrated at 102, including a chromatographic column 104, is supplied to an input port 108 of the sample supply element 106. The sample material supplied at the input port 108 is referred to as the "effluent" and represents the output of the chromatographic column 104. The sample supply element 106 also includes a port 112 through which a supply of hydrogen is supplied, and a port 114 through which a supply of oxygen or air is provided. The sample supply element 106 also includes a burner element 116 to provide a flame 118. In accordance with the operation of the flame photometric detector 100, the sample introduced via the chromatographic column 104 is volatized in a hydrogen rich flame 118. Heating the sample in the hydrogen rich flame 118 excites the molecules in the sample and if present, causes excited species of sulfur ($S_2$ in this example) and phosphorous (HPO in this example) to be formed from the effluent.

The flame 118 burns within a chamber 126, which includes an exhaust port 122. The exhaust port 122 is configured to carry away all combustion by-products from the chamber 126. The chamber 126 also includes a chemiluminescence region 128. The chemiluminescence region 128 is the area within the body 146 of the flame photometric detector 100 in which the sample volatized by the flame 118 forms excited molecules that will be detected by the photomultiplier tube 138. The term chemiluminescence refers to the process by which an excited species of molecule emits light energy in the form of photons at a series of particular wavelengths. As will be described below, the photons pass through the thermal filter 134 and a selective optical filter 150 and are detected and amplified by the photomultiplier tube 138.

A thermal filter 134 separates the chemiluminescence region 128 and the chamber 126 from the selective optical filter 150. In this example, the selective optical filter 150 is removable and interchangeable so that the wavelength of light generated in the chemiluminescence region 128 and passed to the photomultiplier tube 138 can be selectively detected. When the sample is burned in the chamber 126 the sample emits excited species that emit photons at one or more characteristic wavelengths. The selective optical filter 150 filters the light energy impinging thereon, and passes selected wavelengths to the photomultiplier tube 138. The photomultiplier tube 138 receives a high voltage energy source on connection 142 and provides an output on connection 144 to an amplifier and other processing elements (not shown). The photomultiplier tube 138 converts photons to an electrical signal to quantify the concentration of a particular excited species. The photons that impinge on the photomultiplier tube 138 have a characteristic wavelength depending upon the material that has undergone a chemiluminescent reaction in region 128. In this manner, the flame photometric detector 100 can determine, via the characteristic wavelength of the light energy that impinges on the photomultiplier tube 138, whether a particular element is present in the sample.

In a typical application, the flame photometric detector 100 is used to detect the presence of sulfur and/or phosphorous in a sample. When excited due to the chemiluminescent reaction, sulfur becomes a molecular species referred to as "$S_2$," and phosphorous becomes a molecular species referred to as "HPO."

In a conventional flame photometric detector, the optical filter has historically been designed as a narrow band-pass optical filter, which is designed to pass a small portion of the electromagnetic spectrum that is characteristic of the material sought to be detected. In accordance with an embodiment of the invention, the selective optical filter 150 is fabricated as a broad band-pass optical filter and in an alternative embodiment, as a plurality of selective band-pass optical filters having selective transmissive and non-transmissive regions. Until a broad band-pass selective optical filter was implemented by the inventors, it was thought that such an optical filter would be incapable of detecting the $S_2$ and the HPO species with sufficient selectivity. However, it has been discovered that historical concerns about the expected poor filter selectivity when using a broad band-pass optical filter are not valid. In accordance with an embodiment of the invention, a broad band-pass selective optical filter provides both high selectivity and high sensitivity for detecting both the $S_2$ and the HPO species.

Figure 2:
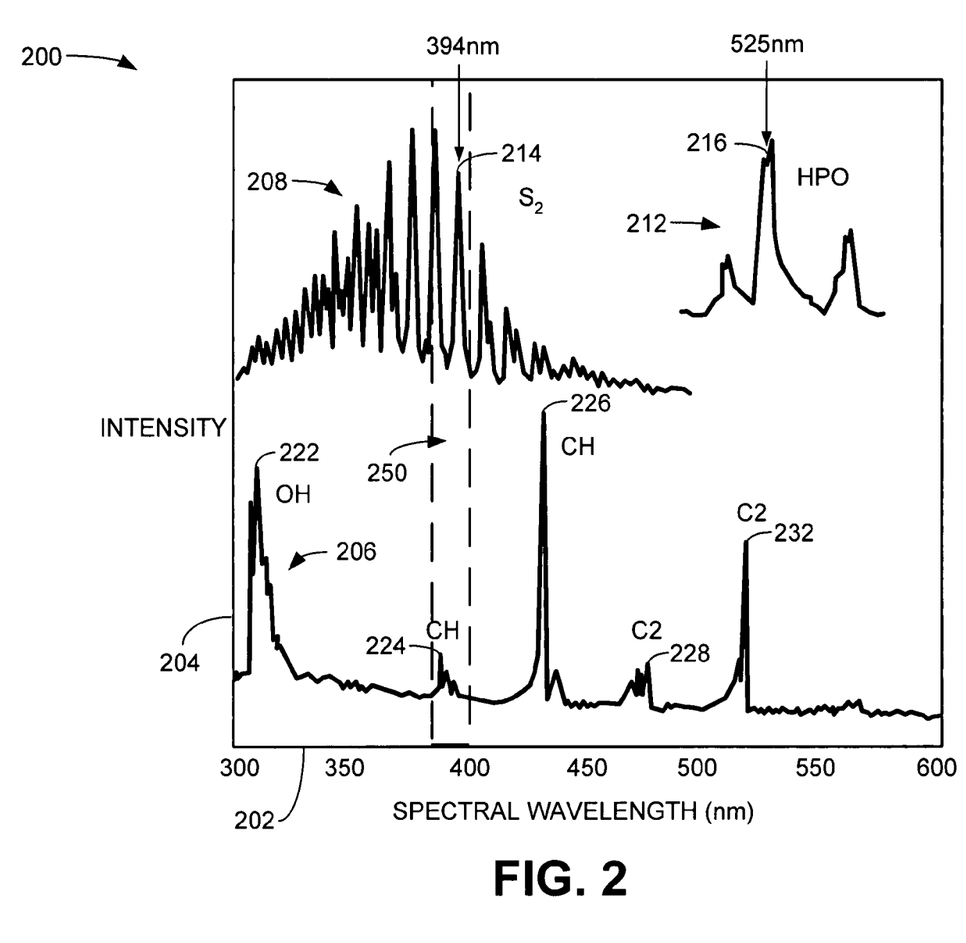
FIG. 2 is a graphical illustration showing the spectral wavelength and filter transmission band of a conventional optical filter.

FIG. 2 is a graphical illustration 200 showing the spectral wavelength and filter transmission band of a conventional optical filter. The horizontal axis 202 represents spectral wavelength in nanometers (nm) and the vertical axis 204 represents signal intensity through an optical filter. The trace 206 illustrates an interference signal containing multiple peaks 222, 224, 226, 228 and 232 of hydrocarbon or OH that is present in most combusted samples. The trace 208 represents the optical response of sulfur after it is combusted by the flame photometric detector 100, and the trace 212 represents the optical response of phosphorous after it has been combusted by the flame photometric detector 100. The curve 208 includes a plurality of characteristic wavelengths (364 nm, 374 nm, 384 nm and 394 nm (illustrated in FIG. 2)) of the excited $S_2$ molecule and the curve 212 includes a characteristic wavelength (525 nm) of the excited HPO molecule.

The region indicated at 250 illustrates a narrow optical transmission band that includes the 394 nanometer wavelength that is one of the characteristic wavelengths of the excited $S_2$ sulfur molecule. The peak illustrated at point 214 represents the 394 nm characteristic emission of the sulfur $S_2$ molecule while the peak 216 illustrates the characteristic 525 nanometer wavelength emission of the phosphorous HPO. In this example, a conventional narrowband optical filter would pass only the 394 nm $S_2$ characteristic wavelength.

Figure 3:
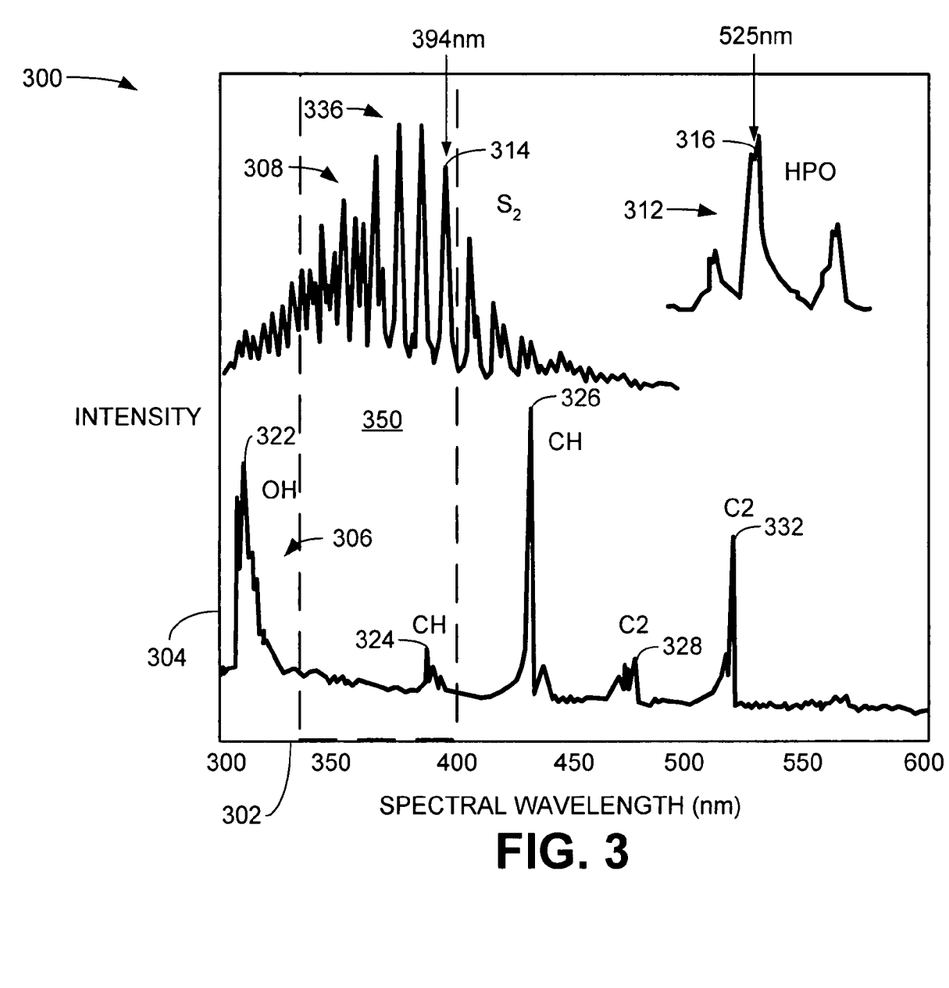
FIG. 3 is a graphical illustration showing the optical characteristics of a selective optical filter constructed in accordance with an embodiment of the invention.

FIG. 3 is a graphical illustration 300 showing the optical characteristics of a selective optical filter constructed in accordance with an embodiment of the invention. The horizontal axis 302 represents spectral wavelength in nanometers, and the vertical axis 304 represents signal intensity through the selective optical filter. The trace 306 represents interfering signals including a plurality of hydrocarbon and OH peaks 322, 324, 326, 328 and 332, the trace 308 represents the optical response of the $S_2$ sulfur molecule after it is combusted by the flame photometric detector 100, and the trace 312 represents the optical response of the HPO phosphorous molecule after it is combusted by the flame photometric detector 100. The curve 308 includes a plurality of characteristic wavelengths (364 nm, 374 nm, 384 nm and 394 nm) of the excited $S_2$ molecule and the curve 312 includes a characteristic wavelength (525 nm) of the excited HPO molecule.

In accordance with an embodiment of the invention, the selective optical filter 150 has a broad transmissive band illustrated as transmissive region 350. In this example, the transmissive region encompasses wavelengths from approximately 335 to 405 nanometers. This broad band-pass filter characteristic captures most of the characteristic wavelengths of the $S_2$ molecule (364 nm, 374 nm, 384 nm and 394 nm) illustrated generally at 336. Other characteristic wavelengths of the $S_2$ molecule include, for example, 342 nm, 350 nm and 359 nm. The broad band-pass filter characteristic illustrated using transmissive region 350 provides superior signal-to-noise ratio while taking advantage of a broad range of characteristic wavelengths 336 characterizing the $S_2$ sulfur molecule. The selective optical filter 150 is designed to be non-transmissive at wavelengths outside of the transmissive region 350.

Figure 4:
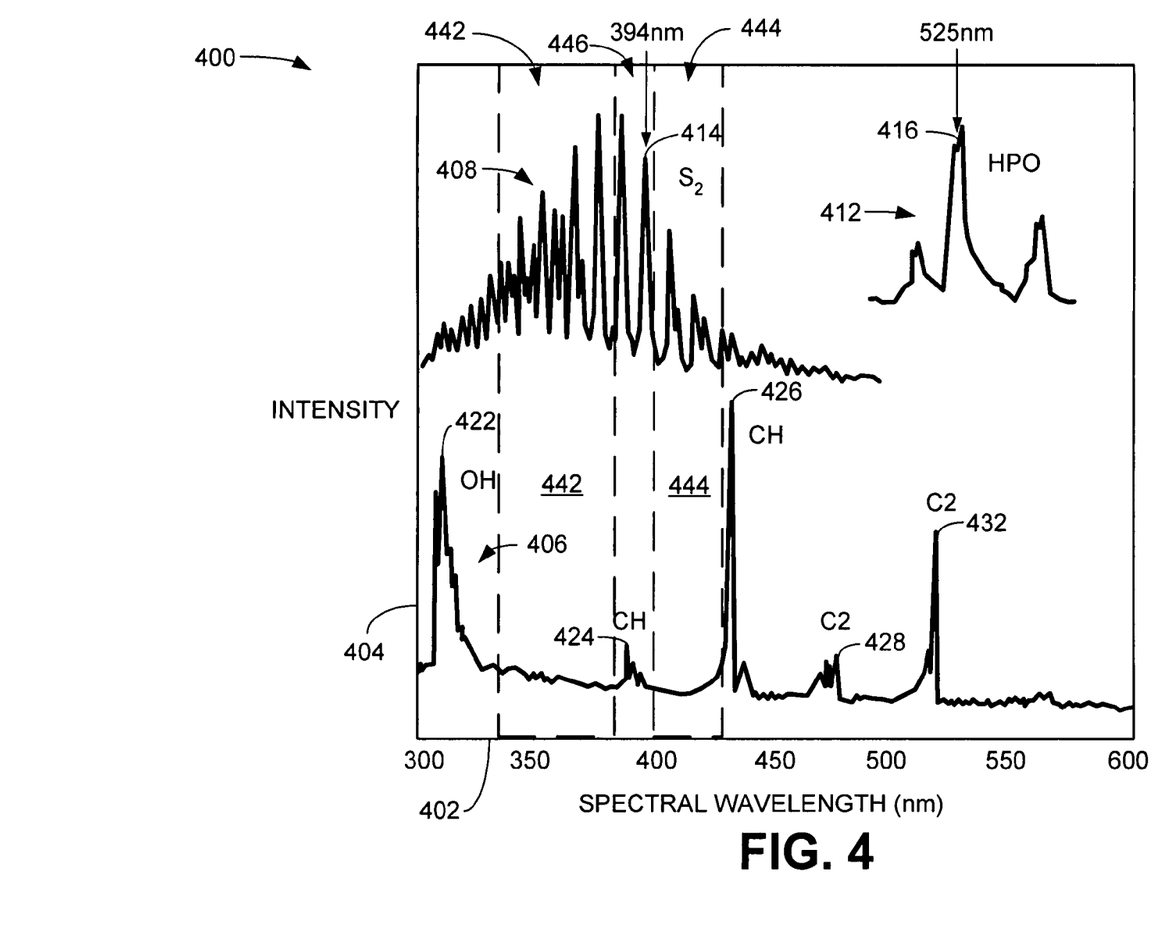
FIG. 4 is a graphical illustration showing the optical characteristics of another embodiment of the selective optical filter.

FIG. 4 is a graphical illustration 400 showing the optical characteristics of another embodiment of the selective optical filter. The horizontal axis 402 represents a spectral wavelength in nanometers and the vertical axis 404 represents signal intensity through the selective optical filter. The trace 406 represents an interfering signal including a plurality of hydrocarbon and OH peaks 422, 424, 426, 428 and 432, the trace 408 represents the response of the $S_2$ sulfur molecule after it is combusted by the flame photometric detector 100, and the trace 412 represents the response of the HPO phosphorous molecule after it is combusted by the flame photometric detector 100. The curve 408 includes a plurality of characteristic wavelengths (364 nm, 374 nm, 384 nm and 394 nm) of the excited $S_2$ molecule and the curve 412 includes a characteristic wavelength (525 nm) of the excited HPO molecule.

The optical filter characteristic of a selective optical filter indicated using the graphical illustration 400 shows a transmissive region 442 and a transmissive region 444 with a non-transmissive region 446 there between. The transmissive region 442 is transmissive in the approximate wavelength region of 335 through 380 nanometers and the transmissive region 444 is transmissive in the approximate wavelength region of 405 through 425 nanometers. The non-transmissive region 446 occupies an approximate spectral wavelength encompassing 385 through 400 nanometers. In this example, there is an approximate 5 nm region between the non-transmissive region 446 and the transmissive regions 442 and 444 that is considered neither transmissive nor non-transmissive due to optical filter performance characteristics.

The non-transmissive region 446 is referred to as a "notch" in that the wavelengths therein are notched out of the filter response. As shown in FIG. 4, the non-transmissive region 446 encompasses the hydrocarbon response of the interfering trace 406 shown at point 424. By notching out the hydrocarbon response at this wavelength, both high selectivity and high sensitivity to detecting the $S_2$ sulfur molecule at the characteristic wavelengths 342 nm, 350 nm, 359 nm, 364 nm and 374 nm are provided by the selective optical filter 150.

Figure 5:
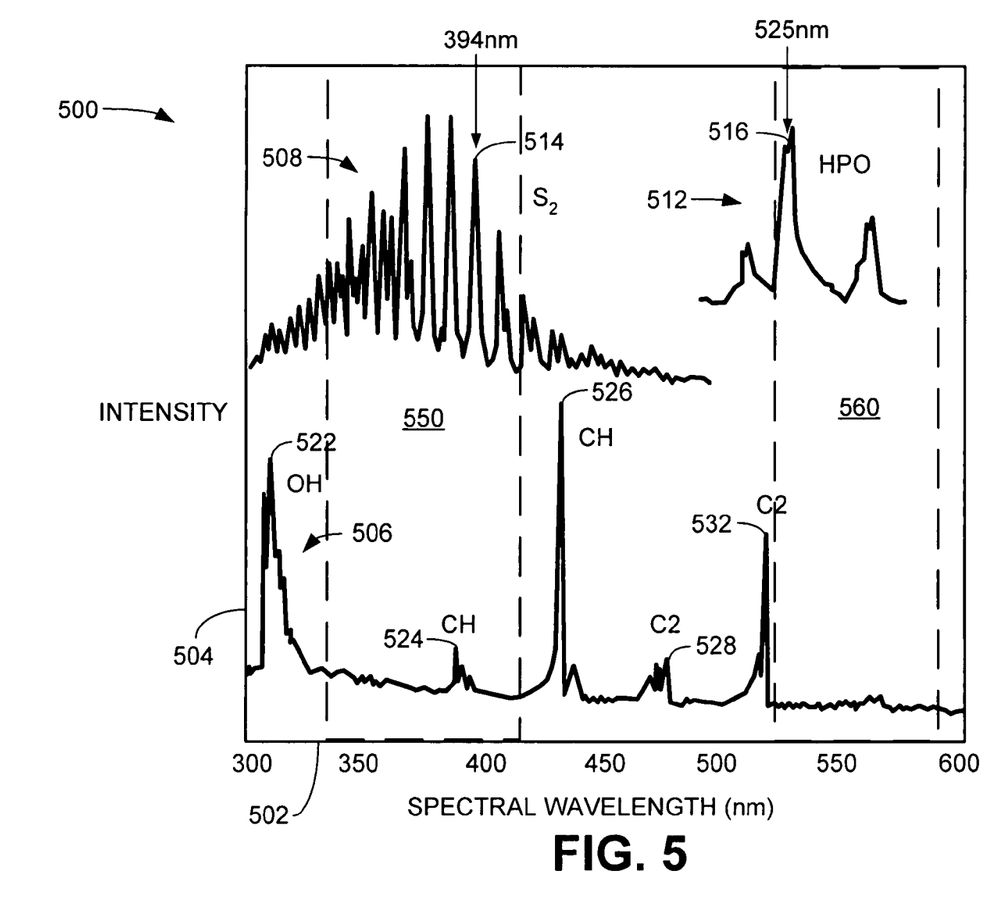
FIG. 5 is a graphical illustration showing the optical characteristics of another embodiment of the selective optical filter.

FIG. 5 is a graphical illustration 500 showing the optical characteristics of another embodiment of the selective optical filter. The horizontal axis 502 represents spectral wavelength in nanometers and the vertical axis 504 represents signal intensity through the selective optical filter. The trace 506 represents an interfering signal including a plurality of hydrocarbon and OH peaks 522, 524, 526, 528 and 532, the trace 508 represents the response of the $S_2$ sulfur molecule after it is combusted by the flame photometric detector 100, and the trace 512 represents the response of the HPO phosphorous molecule after it is combusted by the flame photometric detector 100. The curve 508 includes a plurality of characteristic wavelengths (364 nm, 374 nm, 384 nm and 394 nm) of the excited $S_2$ molecule and the curve 512 includes a characteristic wavelength (525 nm) of the excited HPO molecule. Other characteristic wavelengths of the HPO molecule may also be detected.

The filter response shown in FIG. 5 includes a transmissive region 550 and a transmissive region 560. The transmissive region 550 encompasses the approximate wavelengths of 335 through 405 nanometers while the transmissive region 560 encompasses the approximate wavelengths of 520 through 580 nanometers. In this manner, a single selective optical filter can provide optical sensitivity and selectivity for detecting both the $S_2$ sulfur molecule and the HPO phosphorous molecule. As shown in FIG. 5, the characteristic wavelength emission (364 nm, 374 nm, 384 nm and 394 nm) of the excited $S_2$ molecule and the characteristic 525 nanometer wavelength emission of the excited HPO phosphorous molecule are easily captured within the transmissive regions 550 and 560, respectively, while interfering hydrocarbon and OH signals illustrated at 522, 526, 528 and 532 lie outside of the transmissive regions 550 and 560.

Figure 6:
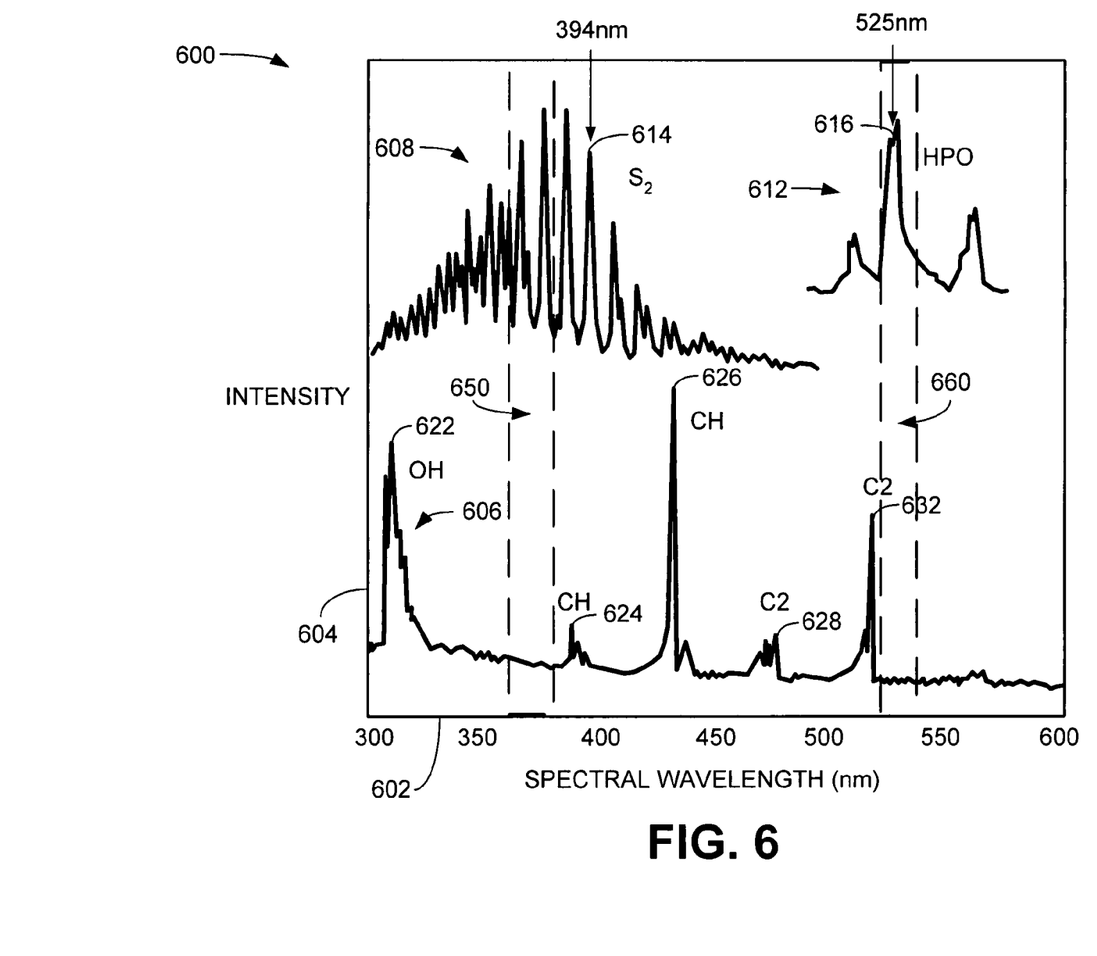
FIG. 6 is a graphical illustration showing the optical characteristics of another embodiment of the selective optical filter.

FIG. 6 is a graphical illustration 600 showing the optical characteristics of another embodiment of the selective optical filter. The horizontal axis 602 represents spectral wavelength in nanometers and the vertical axis 604 represents signal intensity through the selective optical filter. The trace 606 represents an interfering signal including a plurality of hydrocarbon and OH peaks 622, 624, 626, 628 and 632, the trace 608 represents the response of the $S_2$ sulfur molecule after it is combusted by the flame photometric detector 100, and the trace 612 represents the response of the HPO phosphorous molecule after it is combusted by the flame photometric detector 100. The curve 608 includes a plurality of characteristic wavelengths (364 nm, 374 nm, 384 nm and 394 nm) of the excited $S_2$ molecule and the curve 612 includes a characteristic wavelength (525 nm) of the excited HPO molecule.

The optical response of the selective optical filter shown in FIG. 6 includes transmissive region 650, which encompasses an approximate wavelength range of 355 through 375 nanometers and the transmissive region 660, which encompasses an approximate wavelength range of 520 through 540 nanometers. The transmissive region 650 is selectively defined to omit the hydrocarbon peak located at point 624 and the transmissive region 660 is selectively defined to omit the hydrocarbon peak located at point 632. However, the transmissive region 650 still includes sufficient wavelength range to capture the 364 nm and the 374 nm $S_2$ molecule peaks and the 525 nm HPO molecule peak.

Figure 7:
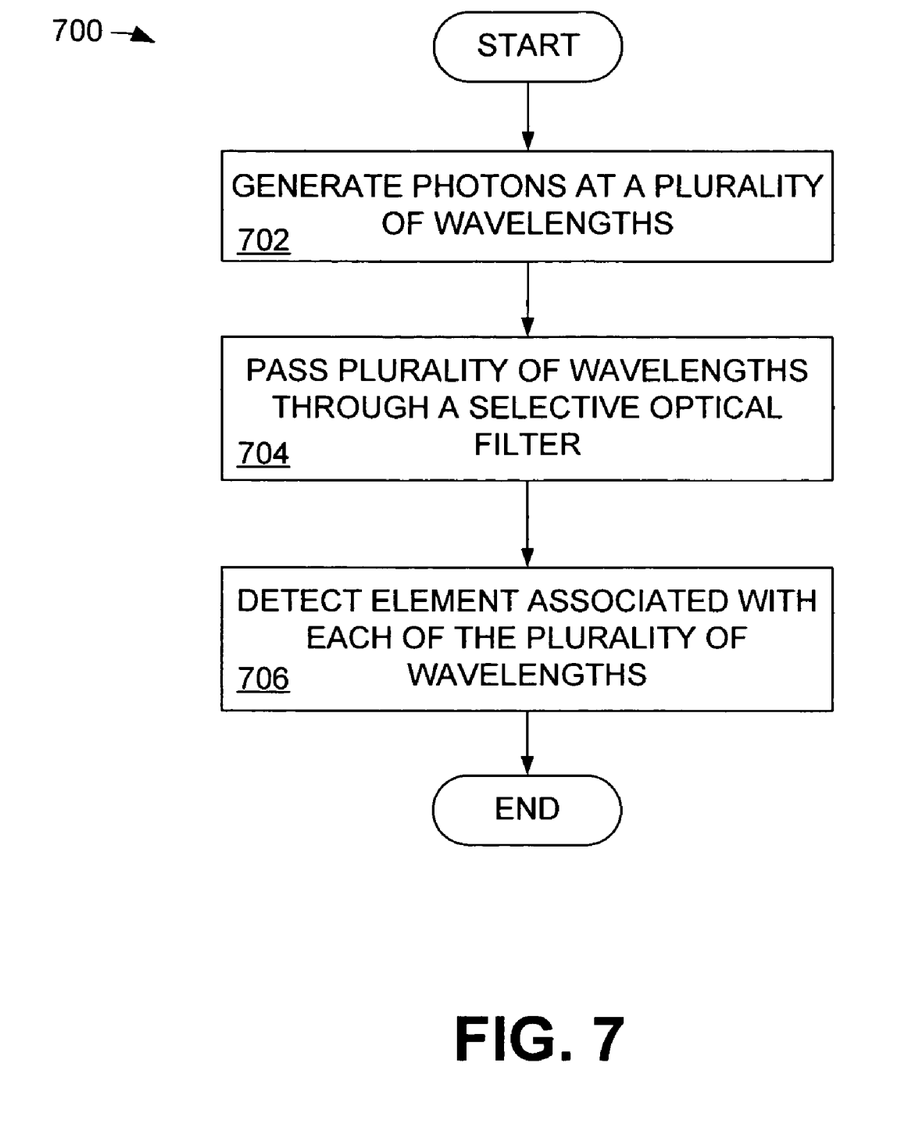
FIG. 7 is a flow chart illustrating a method for selectively detecting optical signals.

FIG. 7 is a flow chart 700 illustrating a method for selectively detecting optical signals. In block 702, the flame photometric detector 100 generates photons from a sample at a plurality of different wavelengths. In block 704, the plurality of wavelengths are passed through a single selective optical filter 150. In block 706, the photomultiplier tube 138 detects an element associated with each of the plurality of wavelengths.

The foregoing detailed description has been given for understanding exemplary implementations of the invention in the gas phase only and no unnecessary limitations should be understood therefrom as modifications will be obvious to those skilled in the art without departing from the scope of the appended claims and their equivalents.

We claim:

1. A flame photometric detector, comprising:
   a burner assembly configured to combust a sample of an effluent in a non-pulsed flame, the combusted sample emitting at least one excited molecule;
   a single selective optical filter configured to pass at least a first band of selected optical wavelengths, wherein the first band of selected optical wavelengths is within a range of approximately 335 through 405 nm and is bounded by non-transmissive regions, and wherein the first band of selected optical wavelengths includes an at least 20 nm range of wavelengths; and
   a photomultiplier tube configured to i) receive and amplify all of the selected optical wavelengths passed by the single selective optical filter, and ii) produce an electrical signal from which a presence of at least an excited sulfur $S_2$ molecule in the combusted sample is detected.

2. A flame photometric detector, comprising:
   a burner assembly configured to combust a sample of an effluent in a non-pulsed flame, the combusted sample emitting at least one excited molecule:
   a single selective optical filter configured to simultaneously pass at least a first band of selected optical wavelengths and a second band of selected optical wavelengths, wherein the first band of selected optical wavelengths is a band of approximately 335 through 380 nm and is bounded by non-transmissive regions, wherein the second band of selected optical wavelengths is a band of approximately 405 through 425 nm and is bounded by non-transmissive regions, and wherein one of the non-transmissive regions is approximately 385 through 400 nm; and
   a photomultiplier tube configured to i) receive and amplify all of the selected optical wavelengths passed by the single selective optical filter, and ii) produce an electrical signal from which a presence of at least an excited sulfur $S_2$ molecule in the combusted sample is detected.

3. The flame photometric detector of claim 1, wherein the single selective optical filter is configured to simultaneously pass the first band of selected optical wavelengths and a second band of selected optical wavelengths, the second band of selected optical wavelengths including at least one characteristic wavelength of an optical response of an excited phosphorous HPO molecule.

4. The flame photometric detector of claim 1, wherein the single selective optical filter is configured to simultaneously pass the first band of selected optical wavelengths and a second band of selected optical wavelengths, wherein the second band of selected optical wavelengths is a band of approximately 520 through 540 nm.

5. The flame photometric detector of claim 1, wherein the first band of selected optical wavelengths is a band of approximately 335 through 405 nm.

6. The flame photometric detector of claim 5, wherein the single selective optical filter is configured to simultaneously pass the first band of selected optical wavelengths and a second band of selected optical wavelengths, wherein the second band of selected optical wavelengths is a band of approximately 520 through 580 nm.

7. The flame photometric detector of claim 1, wherein the single selective optical filter is configured to simultaneously pass the first band of selected optical wavelengths and a second band of selected optical wavelengths, the second band separated from the first band by a non-transmissive region of the single selective optical filter.

8. The flame photometric detector of claim 1, wherein the single selective optical filter is removable and interchangeable with another filter.

9. A flame photometric detector, comprising:
a burner assembly configured to combust a sample of an effluent, the combusted sample emitting at least one excited molecule;
a single selective optical filter configured to simultaneously pass a first band of selected optical wavelengths and a second band of selected optical wavelengths, the single selective optical filter having a non-transmissive region between the first band and the second band; and
a photomultiplier tube configured to i) receive and amplify all of the selected optical wavelengths passed by the single selective optical filter, and ii) produce an electrical signal from which a presence of at least one of the at least one excited molecule is detected.

10. The flame photometric detector of claim 9, wherein:
the first band of the single selective optical filter passes at least one characteristic wavelength of an optical response of an excited sulfur $S_2$ molecule;
the second band of the single selective optical filter passes at least one other characteristic wavelength of the optical response of the excited sulfur $S_2$ molecule; and
the photomultiplier tube produces an electrical signal from which a presence of the excited sulfur $S_2$ molecule in the combusted sample is detected.

11. The flame photometric detector of claim 10, wherein the first band of the single selective optical filter passes wavelengths in a range of approximately 335 through 380 nm, and the second band of the single selective optical filter passes wavelengths in a range of approximately 405 through 425 nm.

12. The flame photometric detector of claim 9, wherein:
the first band of the single selective optical filter passes at least one characteristic wavelength of an optical response of an excited sulfur $S_2$ molecule;
the second band of the single selective optical filter passes at least one characteristic wavelength of an optical response of an excited phosphorous HPO molecule; and
the photomultiplier tube produces an electrical signal from which presences of the excited sulfur $S_2$ and excited phosphorous HPO molecules in the combusted sample are detected.

13. The flame photometric detector of claim 12, wherein the first band of the single selective optical filter passes wavelengths in a range of approximately 335 through 405 nm, and the second band of the single selective optical filter passes wavelengths in a range of approximately 520 through 580 nm.

14. The flame photometric detector of claim 12, wherein the first band of the single selective optical filter passes wavelengths in a range of approximately 355 through 375 nm, and the second band of the single selective optical filter passes wavelengths in a range of approximately 520 through 540 nm.

15. The flame photometric detector of claim 1, wherein the first band of selected optical wavelengths is a band of approximately 355 through 375 nm.

16. The flame photometric detector of claim 1, wherein the first band of selected optical wavelengths is a band of approximately 335 through 380 nm.

* * * * *